US008676302B2

(12) United States Patent
Wang et al.

(10) Patent No.: US 8,676,302 B2
(45) Date of Patent: Mar. 18, 2014

(54) SYSTEMS AND METHODS FOR MULTI-SPECTRAL BIOLUMINESCENCE TOMOGRAPHY

(75) Inventors: Ge Wang, Blacksburg, VA (US); Alexander X. Cong, Blacksburg, VA (US); Weimin Han, Coralville, IA (US); Ming Jiang, Iowa City, IA (US); Haiou Shen, Blacksburg, VA (US); Wenxiang Cong, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 1719 days.

(21) Appl. No.: 11/619,495

(22) Filed: Jan. 3, 2007

(65) Prior Publication Data

US 2007/0244395 A1 Oct. 18, 2007

Related U.S. Application Data

(60) Provisional application No. 60/756,036, filed on Jan. 3, 2006.

(51) Int. Cl.
*A61B 6/00* (2006.01)

(52) U.S. Cl.
USPC .......................................................... 600/476

(58) Field of Classification Search
USPC ................. 600/310, 317, 407, 425, 473, 476; 356/72, 73
See application file for complete search history.

(56) References Cited

U.S. PATENT DOCUMENTS

| | | | |
|---|---|---|---|
| 7,720,526 B1 * | 5/2010 | Modell | 600/476 |
| 2004/0033616 A1 * | 2/2004 | Le | 436/164 |
| 2004/0249260 A1 * | 12/2004 | Wang et al. | 600/407 |

OTHER PUBLICATIONS

Warren et al., "Combined Ultrasound and Fluorescence Spectroscopy for Physico-Chemical Imaging of Atherosclerosis". IEEE Transactions on Biomedical Engineering 42(2) (1 995): 121-1 32.*
Gu et al, Three-dimensional bioluminescence tomography with model-based reconstruction, Optics Express, vol. 12, Issue 17, pp. 3996-4000 (2004.*
Hyperspectral and multispectral bioluminescence optical tomography for small animal imaging, Phys. Med. Biol., 50 (2005) 5421-5441, henceforth referred to as Chaudhari.*
Chaudhari, et al.; "Hyperspectral and Multispectral Bioluminescence Optical Tomography for Small Animal Imaging"; IOP Publishing Ltd.; Phys. Med. Biol., vol. 50; 2005; pp. 5421-5441.

(Continued)

*Primary Examiner* — Unsu Jung
*Assistant Examiner* — Saurel J Selkin
(74) *Attorney, Agent, or Firm* — Smith, Gambrell & Russell

(57) ABSTRACT

Bioluminescent imaging has proven to be a valuable tool for monitoring physiological and pathological activities at cellular and molecular levels in living small animals. Using biological techniques, target cells can be tagged with reporters which generate characteristic photons in a wide spectrum covering the infra-red range. Part of the diffused light can reach the body surface of a subject/specimen (e.g., a small animal), be separated into several spectral bands using optical means, and collected by a sensitive camera. Systems and methods are disclosed herein for multi-spectral bioluminescence tomography (MBLT), in which an image of an underlying 3D bioluminescent source distribution is synergistically reconstructed from spectrally resolved datasets externally measured. This MBLT process involves two or multiple imaging modalities that produce structural information of the object and optical properties of the object as well to enable and improve the quality of MBLT.

15 Claims, 7 Drawing Sheets

(56) References Cited

OTHER PUBLICATIONS

Dehghani, et al.; "Spectrally Resolved Bioluminesence Optical Tomography"; Optics Letters; vol. 31; No. 3; Feb. 1, 2006; pp. 365-367.

Cong, et al.; "Multispectral Bioluminescence Tomography: Methodology and Simulation"; International Journal of Biomedical Imaging; vol. 2006; Nov. 11, 2005; pp. 1-8.

Han, et al.; "Mathematical Study and Numerical Simulation of Multispectral Bioluminescence Tomography"; International Journal Biomedical Imaging; vol. 2006; pp. 1-10.

Han, et al.; "Theoretical and Numerical Analysis on Multispectral Bioluminescence Tomography"; IMA Journal of Applied Mathematics; Dec. 22, 2006; pp. 1-19.

Wang, et al.; "The First Bioluminescence Tomography System for Simultaneous Acquisition of Multiview and Multispectral Data"; International Journal Biomedical Imaging; vol. 2006; pp. 1-8.

* cited by examiner

SYSTEMS AND METHODS FOR MULTI-SPECTRAL BIOLUMINESCENCE TOMOGRAPHY

CROSS-REFERENCE TO RELATED APPLICATION

This application claims priority to U.S. Provisional Application No. 60/756,036 filed Jan. 3, 2006 and hereby incorporated by reference in its entirety.

ACKNOWLEDGEMENT

This invention was made with Government support of Grants No. EB001685 and EB002667, awarded by the National Institutes of Health. The Government has certain rights in this invention.

BACKGROUND

There are many "emission-detection" imaging techniques known in the art based on photon diffusion, such as bioluminescent imaging. However, typical bioluminescent imaging techniques are generally limited to the projective/planar mode. Therefore, three-dimensional structures and localization of an internal light emitting source, such as a bioluminescent source, cannot be resolved in 3D space and time with high quantitative accuracy.

It would therefore be desirable to combine an optical imaging technique, such as a light-emitting source imaging technique, specifically bioluminescence imaging, with one or more independent imaging techniques, such as diffuse optical tomography (DOT), CT/MRI, that allows the evaluation of two and three dimensional anatomical/optical information, to produce a light-emitting source image in 3D space and time.

SUMMARY

The aforementioned light source reconstruction, also referred to as bioluminescence tomography (BLT) in the case of bioluminescence imaging, is generally not uniquely solvable using spectrally mixed data. Embodiments according to this invention utilize appropriate systems and methods that utilize the spectrally resolved data measured on the object surface to improve the image quality. The purpose is primarily but not limited to the development of multi-spectral bioluminescence tomography (MBLT), which can reveal critical information in mouse studies for a large number of biomedical research and applications.

Embodiments according to this invention relate to multi-modality-based systems and methods for determining spectrally dependent optical property distributions and a light-emitting source distribution in 3D space and time, from externally detected signals from optical measurement on the object surface and from one or more tomographic imaging modalities or image processing procedures such as DOT, CT/MRI, digital atlas mapping, etc.

Bioluminescent imaging has proven to be a valuable tool for monitoring physiological and pathological activities at cellular and molecular levels in living small animals. Using biological techniques, target cells can be tagged with reporters encoded several kinds of luciferase enzymes, which generate characteristic photons in a wide spectrum covering the infra-red range. Part of the diffused light can reach the body surface of the small animal, be separated into several spectral bands using appropriate filters, and collected by a sensitive CCD camera. Here aspects of the present invention are directed to multi-modal imaging systems and methods that reconstruct images via fundamental and synergistic utilization of multi-spectral multi-model data.

According to an exemplary embodiment of MBLT, an image volume or model may be reconstructed in a first tomographic modality (such as CT/MRI and other imaging techniques), multi-spectral optical properties from a database may be mapped to the image volume or be determined by DOT, and a light-emitting source distribution may then be reconstructed tomographically from spectrally resolved data measured on the object surface based on the optical properties According to one embodiment, bioluminescence imaging (BLI) and CT/micro-CT combinations may be used, but other system configurations are possible. Some embodiments may include a magnetic resonance imaging (MRI) scanner or micro-MRI scanner in conjunction with a bioluminescence imager. The imaging techniques and algorithms described herein are exemplary only, and other methods of combining data from two or more tomographic scanners may be used.

Some embodiments may be capable of various resolutions depending on scanning times, possess extremely high photon detection sensitivity for mapping gene expression, and/or embody hardware and/or software technology for data acquisition, image reconstruction, registration, visualization and analysis. Some embodiments may have the advantages of being configured to collect data rapidly with a high signal-to-noise ratio and high temporal resolution.

In embodiments directed to bioluminescence, emitted photons can be collected from multiple three-dimensional directions and separated into spectral bands with respect to an animal marked by bioluminescent compounds including reporter luciferases.

According to some embodiments, a CT or micro-CT scanner may be integrated with a bioluminescent imaging system. The bioluminescent imaging system may also be combined with other imaging systems or image processing procedures which provide information regarding the distribution of tissue structures and/or their optical properties in vivo, in situ, or ex vivo.

In alternative embodiments, an object may be serially scanned using each modality in turn. In still further embodiments, the object may be transported between scanning modalities. Optionally, one or more registration marks may be placed on the object to coordinate positions between scanning modalities. The surface of the object may also be optically reconstructed for the registration and/or DOT purpose.

In some embodiments, information associated with x-ray CT imaging, DOT and bioluminescent imaging may be used together to estimate light scatter and/or other optical properties of the anatomy and thereby reconstruct a three-dimensional bioluminescent source image volume registered to corresponding CT or micro-CT images of anatomical and pathological structures. As non-limiting examples, the system may be used to generate images of different kinds of structures, such as bioluminescent sources, lungs and various tumors.

As a non-limiting example, small animal imaging, in particular mouse imaging, may be performed. In other examples, the systems and methods may be used for other biomedical applications where bioluminescent signals are detectable. Some embodiments are especially suited for small animal imaging at molecular levels. For example, genetic activity in a particular organ system may be imaged.

By integrating x-ray and optical imaging, better BLT image quality can be achieved that would not be possible with a stand-alone optical system. From a corresponding x-ray CT image volume or image volume generated by other imaging systems, knowledge of the underlying distribution of optical scatters can be determined. This information is useful in reconstruction of BLT images from BLI data. Alternatively, emitting source distributions may be solved in an integrated manner with reconstruction of optical properties.

According to exemplary embodiments, the combined use of x-ray CT and BLT transforms the nonlinear optical CT problem into an easier linear problem, and can be further regularized via use of spectrally resolved bioluminescent measurement on the mouse body surface. Therefore, the reconstruction of image data from a BLT scanner may be significantly improved.

One embodiment includes a system processor that supports the desired functionality as described in detail below and a system data store (SDS) that stores data associated with the needed functionalities, such as images, measured data and intermediate results. The system processor may be in communication with the SDS via any suitable communication channel(s).

The SDS may include multiple physical and/or logical data stores for storing the various types of information used. Data storage and retrieval functionality can be provided by either the system processor or one or more data storage processors associated with the SDS. The system processor may include one or more processing elements that are adapted or programmed to support the desired image storage, reconstruction and/or other functionality.

Accordingly, one method of image reconstruction includes a variety of steps that may, in certain embodiments, be executed by the environment summarized above and more fully described below or be stored as computer executable instructions in and/or on any suitable combination of computer-readable media. The steps can include but are not limited to performing tomographic reconstruction of an image volume in one modality, mapping optical properties to that volume from a database or estimating the optical properties in vivo using DOT with or without the aid of the first image volume (or model), and performing tomographic reconstruction in another modality based on the mapped optical properties and externally measured spectrally resolved bioluminescent signals Additional advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DETAILED DESCRIPTION

Figure 1:
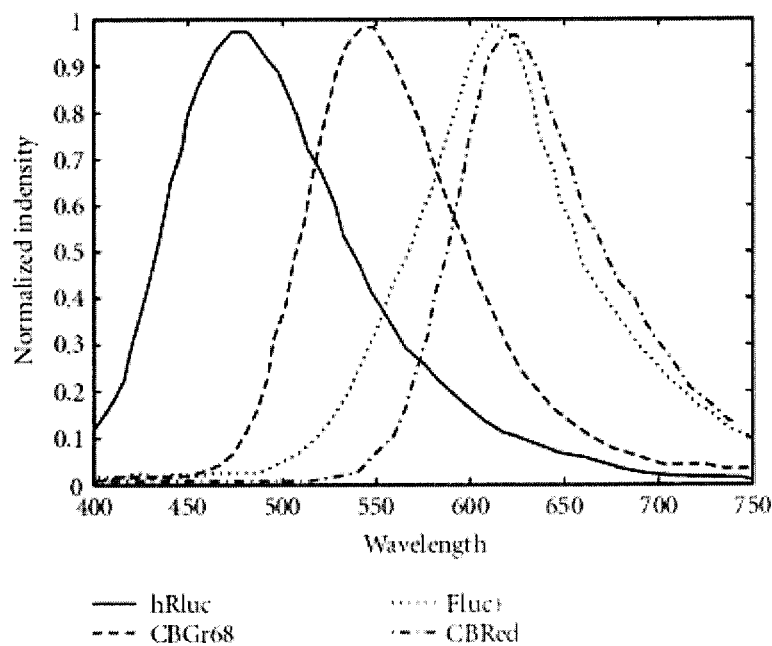
FIG. 1 is an exemplary graph of the spectral peaks of multi-spectral reporters Fluc, CBGr68, CBRed and hRLuc at temperature 37° C., which may be used to practice aspects according to the present invention.

One or more exemplary embodiments are now described in detail herein below and in the attachments hereto. Referring to the drawings, like numbers indicate like parts throughout the views. As used in the description herein and attachments hereto, the meaning of "a," "an," and "the" includes plural reference unless the context clearly dictates otherwise. Also, as used in the description herein and attachments hereto, the meaning of "in" includes "in" and "on" unless the context clearly dictates otherwise. Finally, as used in the description herein and attachments hereto, the meanings of "and" and "or" include both the conjunctive and disjunctive and may be used interchangeably unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Bioluminescent imaging (BLI) is an emerging technology to monitor molecular and cellular activities in vivo using various small animal models. This new modality is extremely sensitive, cost-effective, and non-toxic for investigating a wide variety of diseases such as cancers and facilitating drug development. Bioluminescence tomography (BLT) is a major frontier of BLI. Prior efforts of bioluminescence tomography (BLT) have focused on using a single band of the light spectrum for detection and reconstruction. See, for example, U.S. patent application Ser. No. 10/791,140, now U.S. Pat. No. 8,090,431, "Systems and Methods for Bioluminescent Computed Tomographic Reconstruction" by Wang et al., filed Mar. 2, 2004, which is fully incorporated herein by reference in its entirety. Embodiments according to the present invention relate to systems and methods for reconstructing a bioluminescent source image from the externally measured multi-spectral datasets and tomographic images obtained from one or more other modalities, such as an image volume from CT/micro-CT and/or DOT. Some embodiments may include one or more cameras. These cameras can be arranged, for example, symmetrically, on a spherical surface to detect a light emitting source distribution in three dimensions, or arranged to simultaneously capture multiple views in a spectrally resolved fashion of the subject under consideration, although other arrangements can be contemplated within the scope of this invention. Alternative embodiments may include asymmetrical camera arrangements and/or other three-dimensional surface arrangements. In some embodiments, other optical mechanisms can be used to intercept and direct signals to the cameras including, but not limited to, mirror and/or fiber optic systems.

Some further embodiments may detect and record multi-spectral datasets of bioluminescent emissions and/or fluorescent emissions. This image data, along with associated x-ray CT images of the same object, can be used to reconstruct three-dimensional emission image volumes and register the results to a corresponding x-ray CT/micro-CT image volume of anatomical and pathological structures. In some such embodiments, the bioluminescent (or fluorescent) reconstruction process can be enhanced in a multi-spectrally integrated fashion through the use of knowledge gained from x-ray CT or other anatomic information gathered by use of other imaging devices including, but not limited to, MRI or ultrasound. As a non-limiting example, emitted photons can be collected from multiple directions in three dimensions with respect to a living animal or any other light emitting structure of interest such as specimens marked by bioluminescent reporter luciferases and separated into a plurality of spectral bands using appropriate filters for the purpose of tomography reconstruction of the underlying source distributions. In some embodiments, a lung and/or various tumors may be imaged.

By combining a system for detecting light emission from multiple angles of view simultaneously or sequentially with an imaging modality which allows the evaluation of two and three dimensional structural information, such as micro x-ray CT, the anatomic and/or structural details can be obtained and used to estimate the distribution of light scattering structures. Such a system may enable, as non-limiting examples, both the calculation of the computed tomograms of chemo-luminescence and the linking of the computed tomograms of chemo-luminescence to the anatomic image sets derived from the x-ray CT. In some embodiments, the tomographic reconstruction of bioluminescence can provide important added detail regarding location of reporter gene activity. By knowing the location of reporter gene activity and having images of anatomy, a user can follow the link between gene activation and pathologic processes.

In bioluminescent imaging, target cells are labeled with reporter genes encoding luciferase enzymes in a living small animal. Upon a chemical reaction with a substrate luciferin in the presence of ATP and oxygen, the luciferase releases photons to allow observation of molecular and cellular activities. Luciferase enzymes from, for example, firefly (Fluc), click beetle (CBGr68, CBRed) and *Renilla reniformins* (HRLuc) are often utilized as reporter genes. These luciferase enzymes have different emission spectra. For instance and as shown in FIG. 1, at temperature 37° C., Fluc, CBGr68, CBRed and hRLuc exhibit their spectral peaks of 612 nm, 543 nm, 615 nm and 480 nm, respectively. A tricolor reporter has also been developed, which emits green to red light. These results enable multi-spectral BLT (MBLT), as further described herein, and its biomedical applications.

Bioluminescent photon propagation in biological tissue is subject to both scattering and absorption. A significant number of bioluminescent photons escape from the body surface of a subject specimen or object (e.g., an animal). Using optical filters of different spectral bands, the photons in each spectral band can be captured by one or more highly sensitive CCD cameras. Because the bioluminescence signal decays over a finite period due to its need for intracellular ATP and luciferin substrate, simultaneous acquisition of multiple bioluminescent views are ultimately imperative to improve the image quality, especially when performing MBLT. In combination with the optical data acquisition, the subject (e.g., a mouse) is imaged using one or more independent tomographic imaging modalities, such as x-ray CT/micro-CT and/or DOT. The resultant image volume is segmented into major anatomical components, or more precisely optically homogenous regions, such as heart, lungs, liver, stomach, bones, or their sub-regions, and so on. Each of the components (not necessarily the whole organ) has known optical properties (attenuation, scattering, anisotropy). With such individualized optical property distributions and various domain constraints on the bioluminescent source distribution, bioluminescent data recorded from the animal's surface can be iteratively processed in a spectrally resolved manner to reconstruct the underlying source distribution.

In any band, the photon propagation in the tissue is typically described by the radiative transport equation, as is known in the art. However, a direct solution to the transport equation is not practically affordable due to the computational complexity. Since scattering predominates over absorption in this context, the diffusion equation can be used as a good approximation to the physical process. With optical filter techniques, the optical properties of the tissue can be determined for every spectral band using optical means. For example, diffuse optical tomography (DOT) can be applied to reconstruct the band-specific spatially variable optical parameters. Then, based on the diffusion approximation, MBLT can be formulated as an inverse source problem.

Traditionally, optical tomography utilizes incoming optical, such as near infra-red waves to generate outgoing signals from a scattering object to reconstruct the distribution of the internal optical properties, typically absorption and the reduced scattering coefficients $\mu_a$ and $\mu_s'$. In contrast to this active imaging mode, BLT reconstructs an internal source distribution q from optical measurements on the boundary of a subject or object $\Omega$, utilizing individualized and highly detailed knowledge of the optical properties of $\Omega$ including coefficients $\mu_a$ and $\mu_s'$, which are established from an independently acquired tomographic scan such as x-ray CT/micro-CT of $\Omega$, image segmentation, and optical properties of the structures in $\Omega$.

According to embodiments of the present invention, the imaging accuracy of BLT technology is improved by the utilization of spectrally resolved bioluminescent signals and the incorporation of a priori knowledge, largely based on the anatomical information from, for example, co-registered x-ray CT/micro-CT and the attenuation maps derived optically at the wavelengths of bioluminescence propagation.

It is to be appreciated that there are two meanings attached to the concept of multi-spectral bioluminescence tomography (MBLT). First, the concept involves a single bioluminescent probe that is spatially and spectrally distributed whereby its spectrum is sampled into a number of bands or channels for multi-wavelength measurement and then probe source reconstruction performed. The second concept involves multiple bioluminescent probes that are spatially and spectrally distributed simultaneously whereby in addition to the multi-wavelength sampling and reconstruction, their composite images are decomposed into the individual components corresponding to the probe distributions in the light of known/pre-determined or concurrently estimated differential spectral-profiles. Systems and methods provided herein describe MBLT in the above-defined two senses to facilitate or enable studies on complex processes and interactions labeled by single or multiple bioluminescent probes. By way of non-limiting example, these studies may be performed on, for example, a mouse. Using multiple target-seeking optical reporters and their multi-spectral data in a single experiment, it is highly desirable and feasible to read and unravel the composite molecular/cellular signatures of pathophysiologic events, even in tissues deep within a mouse body.

Typical Storage and Processing Architecture

In one exemplary embodiment, the imaging and reconstruction system includes a system processor potentially including multiple processing elements. The term processing element may refer to (1) a process running on a particular piece, or across particular pieces, of processing hardware, (2) a particular piece of processing hardware, or either (1) or (2) as the context allows. Each processing element can be supported via a standard general purpose processor such as an Intel-compatible processor platforms preferably using at least one CELERON, PENTIUM, XEON, ITANIUM (Intel Corp., Santa Clara, Calif.) or Athlon, Opteron (AMD, Inc., Sunnyvale, Calif.) class processor; alternative processors such as UltraSPARC (Sun Microsystems, Palo Alto, Calif.) or Cell (IBM Corporation, NY) could be used in other embodiments. The system processor, or the one or more processing elements thereof, can include one or more field programmable gate arrays (FPGAs), programmable digital signal processors (DSPs) and/or application specific integrated circuits (ASICs) configured to perform at least a portion of the functionality according to the present invention. In other embodiments, an embedded microprocessor can be used such as, but not limited to, an ARM (ARM, Carlsbad, Calif.) processor core.

In some embodiments, the system processor can include a combination of general purpose processors, ASICs, DSPs and/or FPGAs. In some embodiments, the systems and methods of the present invention, as described above, can be distributed across multiple processing machines such as shared memory MMID (SMP) or distributed memory (MIMD (Cluster). In some such embodiments, aspects of the functionality or portions thereof may be executed in series or in parallel; particular functionality or portions thereof executed a multiplicity of times may also occur in series or parallel.

In a system processor including at least one general or special purpose processor, the general purpose processor typically runs an appropriate operating system such as WINDOWS/NT, WINDOWS 2000 or WINDOWS/XP (Microsoft, Redmond, Wash.), IRIX (Silicon Graphics, Mountain View, Calif.), SOLARIS (Sun Microsystems, Palo Alto, Calif.), or LINUX (or other UNIX variant). In one embodiment, the Windows 2000 operating system is used.

The SDS may include a variety of primary and secondary storage elements. In one embodiment, the SDS can include random access memory (RAM) as part of the primary storage. The SDS can also include secondary storage including single, multiple and/or varied servers and storage elements. For example, the SDS can use an internal hard disk connected to the system bus and the operation system will support the file system on the hard disk. In addition to the local hard disk, an external hard disk, network file system or other network attached storage can be used to expand the secondary storage system.

It will be understood by those skilled in the art that the different information used in the imaging and image reconstruction processes and systems according to the present invention can be logically or physically segregated within a single device serving as secondary storage for the SDS; multiple related data stores accessible through a unified management system, which together serve as the SDS; or multiple independent data stores individually accessible through disparate management systems, which may in some embodiments be collectively viewed as the SDS. The various storage elements that comprise the physical architecture of the SDS may be centrally located or distributed across a variety of diverse locations.

The architecture of the secondary storage of the system data store may vary significantly in different embodiments. In several embodiments, database(s) are used to store and manipulate the data; in some such embodiments, one or more relational database management systems, such as DB2 (IBM, White Plains, N.Y.), SQL Server (Microsoft, Redmond, Wash.), ORACLE (Oracle Corp., Redwood Shores, Calif.), Ingres (Computer Associates, Islandia, N.Y.), MySQL (MySQL AB, Sweden) or Adaptive Server Enterprise (Sybase Inc., Emeryville, Calif.), may be used in connection with a variety of storage devices/file servers that may include one or more standard magnetic and/or optical disk drives using any appropriate interface including, without limitation, ATA/EATA, SATA, and SCSI. In some embodiments, a tape library such as available from Exabyte Corporation (Boulder, Colo.), a storage attached network (SAN) solution such as available from EMC, Inc. (Hopkinton, Mass.), a network attached storage (NAS) solution such as available from Network Appliances (Sunnyvale, Calif.), or combinations thereof may be used. In other embodiments, the data store may use database systems with other architectures such as object-oriented, spatial, object-relational or hierarchical.

Instead of, or in addition to, those organization approaches discussed above, certain embodiments may use other storage implementations such as hash tables or flat files or combinations of such architectures. Such alternative approaches may use data servers other than database management systems such as a hash table look-up server, procedure and/or process and/or a flat file retrieval server, procedure and/or process. Further, the SDS may use a combination of any of such approaches in organizing its secondary storage architecture.

The SDS communicates with the system processor by one or more communication channels. Multiple channels can be involved in some embodiments for supporting communication between processing elements of the system processor and portions of the SDS. Such channels can include without limitation computer network, direct dial-up connection, dedicated connection, direct or indirect connection such as via a bus connection, parallel or serial connection, USB connection, null modem connection or wireless connection utilizing an appropriate communication protocol such as BLUETOOTH, IRDA, IEEE 802.11, or other suitable channel as would be known to those skilled in the art.

All forms of data, including raw, intermediate, and computed can be stored on one or more SDS either temporarily or permanently. In particular, the SDS can store, without limitation, image data, including volumetric image data, reconstruction intermediate data, final reconstructed imaging data, imaging parameters, and reconstruction parameters. Further, the SDS may, in some embodiments, store instructions for performing the various imaging, reconstruction, processing, visualization and analysis tasks, or portions of such tasks.

Methodology

The process of photon propagation in tissue can be formulated as the multi-spectral diffusion approximation to the multi-spectral radiative transport equation under coherent scattering conditions. The coherent scattering condition is an approximation to the complicated realistic light migration process. MBLT can then be formulated as an inverse source problem for the multi-spectral diffusion approximation subject to multi-spectral Cauchy data. Then, characterization of the solution structure for MBLT can be provided. Because any source distribution can be approximated by radial basis functions (RBF), solution uniqueness can be found in details for RBF sources in MBLT. For instance, it can be shown that when a RBF light source is of at least two wavelengths, the solution uniqueness for MBLT can be established for the first time under the following practical conditions: a) the object is piece-wisely homogeneous; b) there are measurements of those two wavelengths on one part of the object surface; c) the effective attenuation coefficients are different for those two wavelengths; d) the light source distributions of those two wavelengths are of the same support and proportional everywhere. Conditions a), b) and c) are practical. Condition d) is based on the following practical reasoning: the lights of both wavelengths are generated by the same probe/target pair and should have the same support; their relative intensities are spatially invariant in proportional to the underlying molecular interaction efficiency where the interaction happens.

A. Diffusion Approximation

The range of light emission peaks for characterized luciferase enzymes is about 400-750 nm. In this spectral range, photons are heavily scattered in the tissue, and the diffusion approximation is quite appropriate to describe the photon propagation. The spectrum can be divided into a number of bands $[w_v, w_{v+1}]$, $v=1, 2, \ldots, \tau$. In each spectral band $[w_v, w_{v+1}]$, the diffusion equation can be applied independently:

$$-\nabla \cdot (D_v(r) \nabla \Phi_v(r)) + \mu_{va}(r) \Phi_v(r) = S_v(r), \; v=1,2,\ldots,\tau, \; (r \in \Omega) \quad (1)$$

where $D_v(r) = (3(\mu_{va}(r) + (1-g)\mu_{vs}(r)))^{-1}$, $\Phi_v(r)$ is the photon density within $[w_v, w_{v+1}]$; $S_v(r)$ the photon density of a bioluminescent source within $[w_v, w_{v+1}]$, $\mu_{va}(r)$ the absorption coefficient within $[w_v, w_{v+1}]$, $\mu_{vs}(x)$ the corresponding scattering coefficient, and g the anisotropy parameter. Since bioluminescent imaging experiments are generally performed in a dark environment, little external photons enter $\Omega$ through its boundary $\partial \Omega$. Taking into account the mismatch between the refractive indices $\gamma$ for the subject and $\gamma'$ for the surrounding medium, the boundary condition is expressed as:

$$\Phi_v(r) + 2A(r) D_v(r)(\eta \cdot \nabla \Phi_v(r)) = 0, \; (r \in \partial \Omega) \quad (2)$$

where $\eta$ is the unit outer normal on $\partial \Omega$, A $(r)=(+R(r))/(1-R(r))$, R (r) depends on the refractive index $\gamma$ of the medium, where $R(r) \approx -1.4399\gamma^{-2} + 0.7099\gamma^{-1} + 0.6681 + 0.0636\gamma$. Finally, with the optical filter for bandpass $[w_v, w_{v+1}]$ the measured quantity is the outgoing flux density on $\partial \Omega$:

$$Q_v(r) = -D_v(r)(\eta \cdot \nabla \Phi_v(r)) = \frac{1}{2A(r)} \Phi_v(r), \; (r \in \partial \Omega), \; v=1, 2, \ldots, \tau \quad (3)$$

B. Image Reconstruction

For each spectral band, the diffusion equation (1) and its boundary condition (2) can be formulated into a matrix equation using the finite-element method as follows:

$$([K_v] + [C_v] + [B_v])\{\Phi_v\} = [F_v]\{S_v\}, \; v=1,2,\ldots,\tau \quad (4)$$

where $\{\Phi_v\}$ and $\{S_v\}$ are the collection of all the nodal values of the photon density $\Phi_v(r)$ and source density $S_v(r)$, respectively. Let $[M_v] = ([K_v] + [C_v] + [B_v])$, where $[M_v]$ is a positive definite matrix. Then, the photon density $\{\Phi_v\}$ can be obtained from Eq. (4), $$\{\Phi_v\} = [M_v]^{-1}[F_v]\{S_v\}, \; v=1,2,\ldots,\tau \quad (5)$$

The reconstruction of the bioluminescent source is to identify the vector $\{S_v\}$ from the photon density $\{\Phi_v^{meas}\}$ measured on the surface. $\{\Phi_v\}$ can be partitioned into measurable boundary data $\{\Phi_v^{meas}\}$ and interior values $\{\Phi_v^{igno}\}$. To regularize the BLT reconstruction, a priori knowledge obtained from bioluminescent measurement as well as biomedical, physiological and anatomical information should be incorporated. As a result, the vector $\{S_v\}$ can be divided into two parts: $\{S^p_v\}$ and $\{S^o_v\}$. $\{S^p_v\}$ corresponds to the permissible region $\Omega_p$ where a bioluminescence source may reside, while $\{S^o_v\}$ corresponds to the forbidden region $\Omega_0$ where there should be no bioluminescence source. Therefore, those columns of $[B_v] = [M_v]^{-1}[F_v]$, $v=1, 2, \ldots, \tau$, that correspond to the vector $\{S^o_v\}$ should be removed, and those rows of $[B_v]$ that correspond to $\{\Phi_v^{igno}\}$ should be removed to obtain $[\bar{B}_v]$. That is, a linear relationship between $\{\Phi_v^{meas}\}$ and $\{S^p_v\}$ is provided:

$$\{\Phi_v^{meas}\} = [\bar{B}_v]\{S^p_v\}, \; v=1,2,\ldots,\tau \quad (6)$$

By performing a spectral analysis, the energy contribution of a bioluminescent source can be e typically corrupted by noise, it is not optimal to determined over the entire spectral interval as represented e, we propose to use the following optimization by $$S^p_v = \omega_v S^t, \text{ where } \sum_{v=1}^{\tau} \omega_v \approx 1, S^t$$

denotes the total photon density, and $S^p_v$ the photon density within $[w_v, w_{v+1}]$. Because the measured bioluminescent data are typically corrupted by noise, it is not optimal to solve for $\{S^t\}$ directly from Eq. (6). Hence, as an example, it is proposed to use the following optimization procedure to find a regularized solution:

$$\min_{0 \le s_i^t \le U_v} \left\{ \sum_{v=1}^{\tau} \|[\bar{B}_v]\{\omega_v S^t\} - \Phi_v^{meas}\|_\wedge + \alpha \eta(\{S^t\}) \right\}, \quad (7)$$

where $U_v$ stands for an upper bound, $s_i^t$ the values in $\{S^t\}$, $\hat{\;}$ a weight matrix, $\|V\|_{\hat{\;}} = V^T \hat{\;} V, \eta$ a stabilizing function, and $\alpha$ the regularization parameter. This is a standard linear least square problem with constrains. Alternatively, other objective functions may be used, including those penalizing the discrepancy between the known spectral characteristics of bioluminescent probes and the counterparts recovered using MBLT, as described more fully in the references cited in this patent application.

Although an iterative method may be most suitable to the image reconstruction task in one embodiment, other image reconstruction methods can be used. Even further, the iterative procedure is only an example, and should not be interpreted as a limiting description.

As far as image reconstruction methods are concerned, it is emphasized that there are multiple options or possibilities. Numerical solutions to the Radiative Transfer Equation or its approximations, including but not limited to the diffusion equation, can be based upon for MBLT. A fast analytic method would be very useful in practice. In one embodiment, an analytic approach based on the Kirchhoff approximation may be adapted for MBLT. Other numerical methods, such as meshfree methods, are also feasible for the same purpose. Finally, MBLT techniques should be coupled with classic and novel image unmixing techniques in the case of reconstructing multiple bioluminescent probes.

Numerical Simulation

A. Spectral Distributions

When target cells are tagged with reporters encoded with any of the four kinds of luciferase enzymes, the cells emit photons in the spectral range about 400-750 nm. Based on the emission spectral distribution, the spectrum may be divided into the at least three regions including about 400 nm-530 nm, about 530 nm-630 nm, and about 630 nm-750 nm. By integrating the intensity over each spectral region, the energy distribution can be approximately quantified as, for example, $\omega_3=0.29$ for 400 nm-530 nm, $\omega_2=0.48$ for 530 nm-630 nm, and $\omega_3=0.23$ for 630 nm-750 nm.

B. Single-Band Reconstruction

Figure 2A:
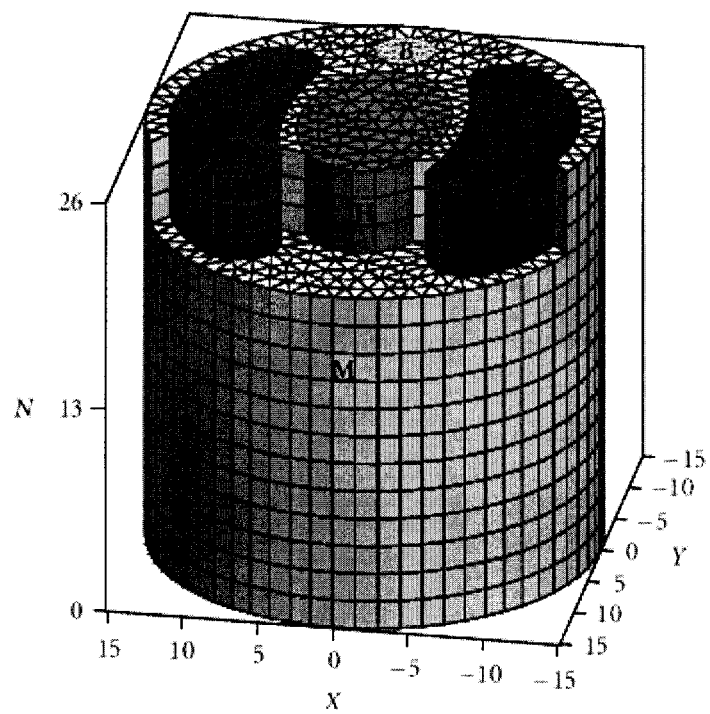
FIGS. 2(a) and 2(b) represents views of an exemplary heterogeneous numerical phantom that contains regions resemble lungs (L), heart (H), muscle (M) and bone (B)
Figure 2B:
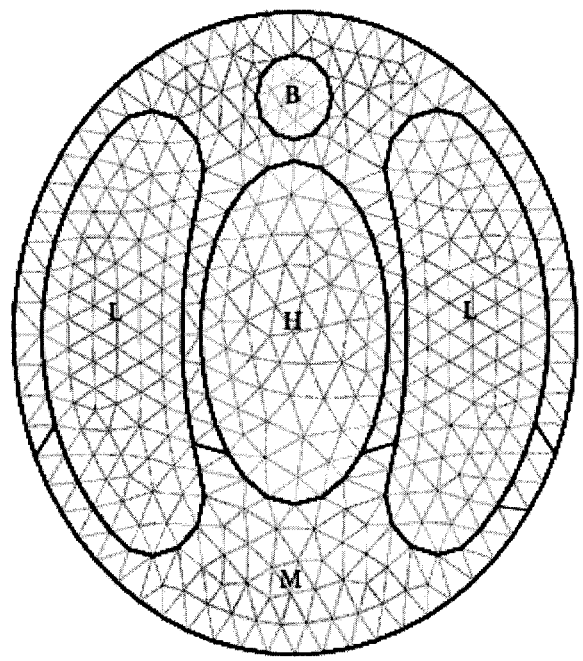
Figure 3A:
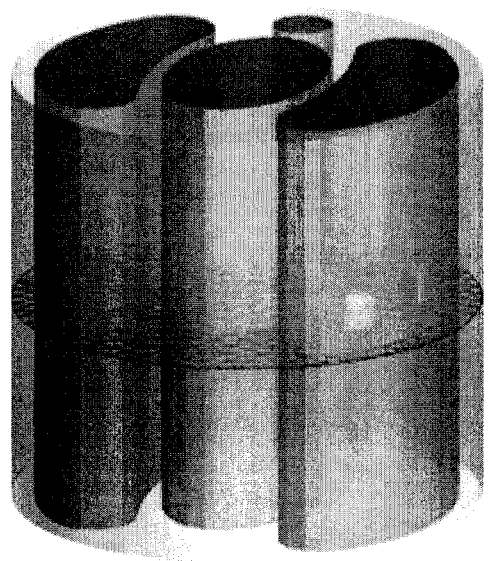
FIG. 3(a) represents exemplary bioluminescent sources embedded in the exemplary heterogeneous numerical phantom of FIGS. 2(a) and 2(b)
Figure 3B:
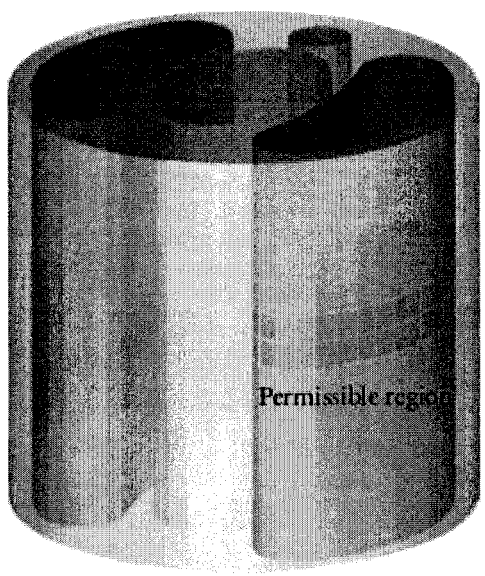
FIG. 3(b) represents a permissible region based on a priori knowledge for the reconstruction of the bioluminescent sources in an embodiment according to the present invention.

FIGS. 2(a) and 2(b) represent an exemplary heterogeneous numerical phantom that contains regions resemble lungs (L), heart (H), muscle (M) and bone (B). This embodiment of a cylindrical phantom has a diameter of 30 mm and height of 26 mm, though other dimensions are contemplated within the scope of this invention. The phantom is discredited into 6576 vertex nodes and 11340 prism elements. Two bioluminescent sources are embedded in the left lung, as shown in FIG. 3(a). The first source located at (−8.66, 3.46, 13.1) and the second one at (−10.21, −3.17, 13.1). Both sources have photon densities of 300 pico-Watts/mm$^3$. The permissible region is selected based on a priori knowledge, as shown in FIG. 3(b). This region contains 308 elements. The optical parameters averaged over the spectral range 400 nm-750 nm for each type of structure in the heterogeneous phantom are listed in Table 1.

TABLE 1

Optical parameters of each type of the structures in the heterogeneous phantom.

| region | $\mu_a$(mm$^{-1}$) | $\mu'_s$(mm$^{-1}$) | g |
|---|---|---|---|
| muscle | 0.0068 | 1.081 | 0.9 |
| lung | 0.0233 | 1.974 | 0.906 |
| heart | 0.0104 | 1.008 | 0.91 |
| bone | 0.0001 | 0.060 | 0.98 |

Figure 4A:
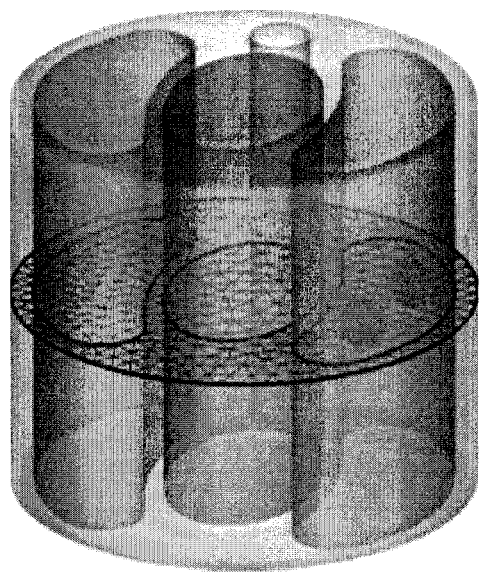
FIG. 4(a) illustrates the reconstructed locations of the bioluminescent sources using a single-band algorithm.
Figure 5A:
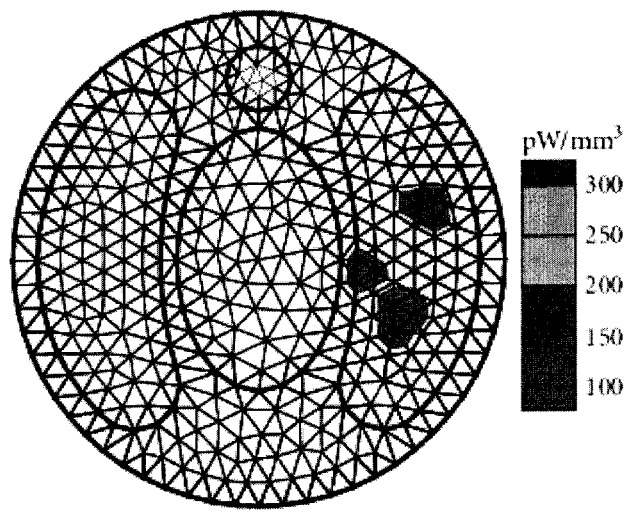
FIG. 5(a) illustrates photon densities of bioluminescent sources reconstructed using a single-band algorithm.

In an exemplary experiment, simulated measurement data on 1024 detector points on the phantom side surface can be generated according to the finite element forward model. Measurement data can be corrupted with, for example, approximately 20% Gaussian noise to simulate measurement uncertainty. First, source reconstruction can be performed using a single-band BLT algorithm. The reconstructed locations of sources using single-band BLT are shown in FIG. 4(a). The photon densities of sources reconstructed using the single-band algorithm are shown in FIG. 5(a). Quantitative data on the reconstruction are shown in Table 2.

TABLE 2

Reconstruction results obtained using the single-band and multi-band algorithms, respectively.

| | single-band reconstruction | | multi-band reconstruction | |
|---|---|---|---|---|
| source | photon density (pW/mm$^3$) | error | photon density (pW/mm$^3$) | error |
| source 1 | 183.06' | 39.0% | 195.69 | 34.8% |
| source 2 | 194.58 | 35.1% | 236.12 | 21.39% |

C. Multi-Band Reconstruction

In one example, multi-spectral BLT reconstruction can be performed using the same numerical model described above in relation to single band reconstruction. Various optical parameters (absorption, scattering) are assigned to different regions of the numerical heterogeneous phantom according to the spectral bands of interest, as listed in Table 3.

TABLE 3

Optical parameters for each type of the structures in the phantom in the bands of interest.

| Region | $\mu_a$(mm$^{-1}$) | $\mu'_s$(mm$^{-1}$) | g |
|---|---|---|---|
| wavelength 630 nm-750 nm | | | |
| Muscle | 0.0052 | 1.081 | 0.90 |
| Lung | 0.0103 | 1.974 | 0.906 |
| Heart | 0.0078 | 1.008 | 0.91 |
| Bone | 0.0001 | 0.060 | 0.98 |
| wavelength 530 nm-630 nm | | | |
| Muscle | 0.0068 | 1.031 | 0.9 |
| Lung | 0.0233 | 1.880 | 0.906 |
| Heart | 0.0104 | 0.986 | 0.91 |
| Bone | 0.0001 | 0.060 | 0.98 |
| wavelength 400 nm-530 nm | | | |
| Muscle | 0.0088 | 1.001 | 0.9 |
| Lung | 0.0423 | 1.833 | 0.906 |
| Heart | 0.0300 | 0.954 | 0.91 |
| Bone | 0.0001 | 0.060 | 0.98 |

Figure 4B:
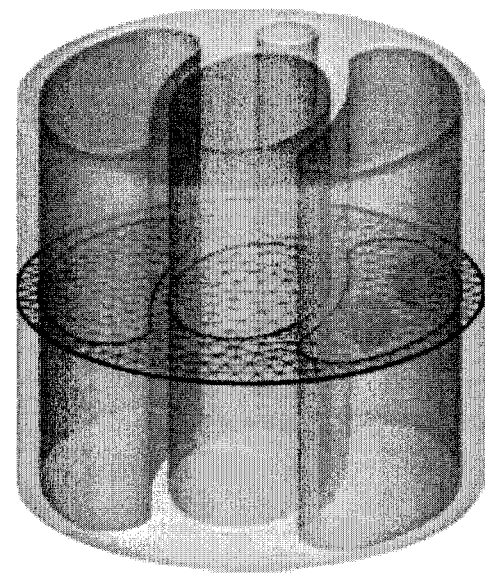
FIG. 4(b) illustrates the reconstructed locations of the bioluminescent sources using the multi-spectral algorithm in an embodiment according to the present invention.
Figure 5B:
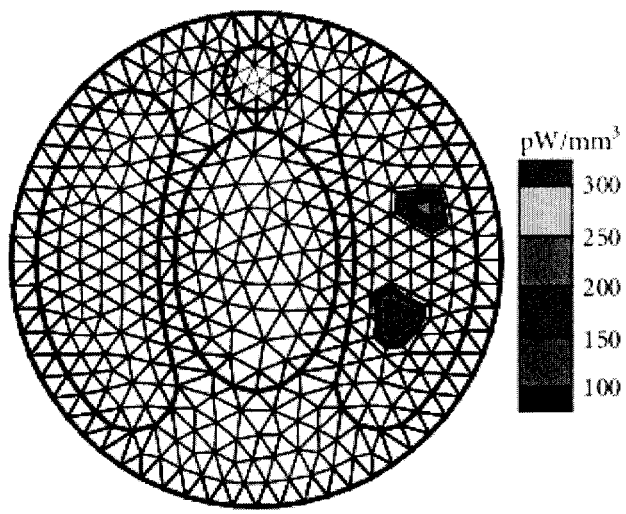
FIG. 5(b) illustrates photon densities of bioluminescent sources reconstructed using a multi-spectral algorithm in an embodiment according to the present invention.

Three measurement datasets on the 1024 detector points on the phantom side surface can be similarly generated for spectral ranges 400-530 nm, 530-630 nm, and 630-750 nm, respectively. The datasets can also be corrupted with approximately 20% Gaussian noise. Then, the three simulated datasets can be taken into the multi-band/multi-spectral reconstruction of the source distribution using the image reconstruction method described above. The reconstructed locations of the sources are shown in FIG. 4(b). The photon densities of the sources reconstructed using the multi-spectral algorithm are shown in FIG. 5(b). The multi-band reconstruction is quantitatively compared to the single-band reconstruction in Table 2.

Multi-Spectral Bioluminescence Tomography System

Figure 6A:
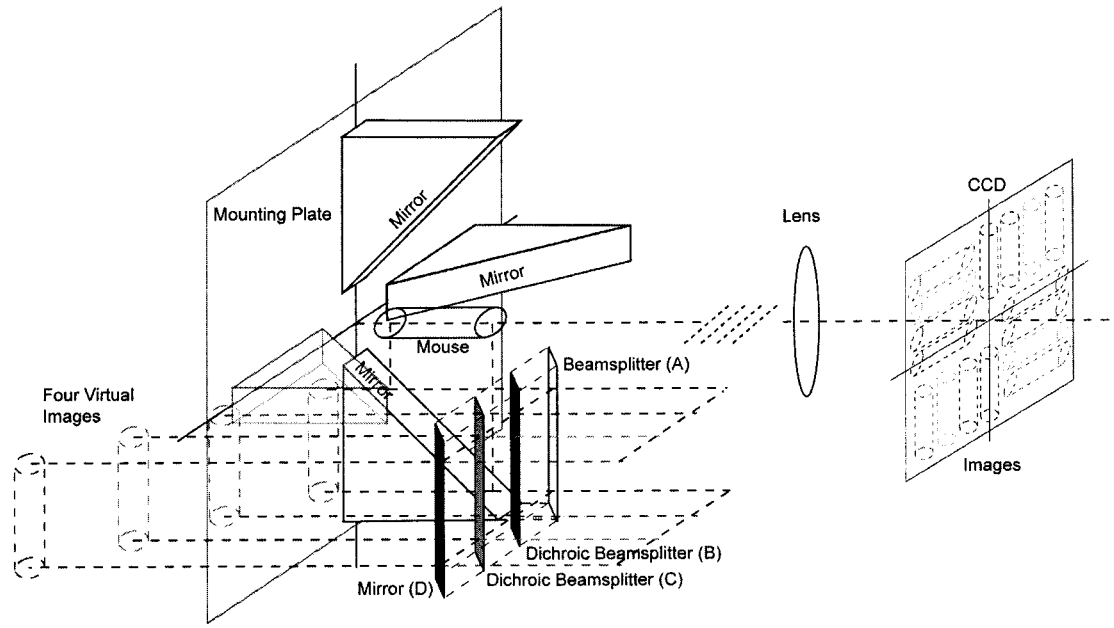
FIG. 6(a) is an illustration of an exemplary MBLT system in an embodiment according to the present invention.

Multi-spectral bioluminescence tomography (MBLT) refers to reconstruction of distributions of single or multiple bioluminescent probes in an integrated fashion. FIG. 6(a) is an illustration of an exemplary MBLT system comprised of five components: multi-view subsystem, multi-spectral subsystem, image acquisition subsystem, a diffuse optical tomography (DOT) subsystem (not shown in FIG. 6(a), 6(b) or 6(c)) and a reconstruction engine (further described herein).

A. Multi-View Subsystem

The multi-view subsystem shown in FIG. 6(a) includes a mounting plate, four mirror stages, and four mirrors. The aluminum mounting plate is, in this instance, a square of about 24 cm side length and about 10 mm thickness, though other sizes and materials are contemplated within the scope of this invention. The aluminum mirror stages are right-angle blocks of about 10 cm side length and about 3 cm thickness, though other sizes and materials are also contemplated within the scope of this invention. The triangular blocks are mounted on the mounting plate substantially symmetrically around the mouse, which is held in an optically transparent cylindrical (as available from, for example, Syntec Optics of Pavilion, NY) mouse holder of radius about 12.5 mm and length about 10 cm. Four rectangular silver coating front mirrors (Thorlabs Inc, Newton, N.J.) of size approximately 14×3 cm² are attached to each of the four hypotenuse surfaces of the mirror stages. The four views of the mouse in the mirrors are parallel to the mounting plate surface. If the mouse maintains in the center of the four mirrors, the four images of the mouse are in the same plane for the camera to focus on all of them simultaneously. To keep the mouse holder in position, it can be attached to the mounting plate with an X-Y flexure stage, which can move the mouse holder within, for example, approximately a 5 mm range along each axis.

B. Multi-Spectral Subsystem

To equip the multi-view subsystem with a multi-spectral imaging capability, a multi-spectral subsystem is added in front of the multi-view subsystem. Since the four views of the multi-view subsystem described above are substantially symmetric, only one optical path is shown in the view of FIG. 6(a). A plane beam splitter (A) (Edmund Optics Inc., Barrington, N.J.) splits light emitted from mouse into two parts: about 25% being directly transmitted to the CCD camera, and about 75% reflected to a dichroic beam splitter (B) (Green-Red dichroic plate beam splitter, Edmund Optics Inc.). The dichroic beam splitter (B) reflects the signal in 530-595 nm wavelengths directly to the CCD camera and transmits the rest light to another dichroic beam splitter (C) (Red-NIR dichroic plate beam splitter, Edmund Optics Inc.). The dichroic beam splitter (C) reflects the signal in 595-664 nm wavelengths to the CCD camera and transmits the signal in the 664-726 nm band to a silver coating front mirror (D) (Thorlabs Inc.). The mirror (D) reflects the rest of the spectrum to the CCD camera. In one embodiment, all the beam splitters, dichroic beam splitters, and mirrors have the same size of approximately 10×5 cm², though other sizes are contemplated within the scope of the invention In FIG. 6(a), there are four virtual images for each view, corresponding to multi-spectral datasets in wavelength bands 500-750 nm, 530-595 nm, 595-664 nm and 664-726 nm ranges, respectively. Hence, in the embodiment of FIG. 6(a), there are a total of 16 images imposed on the CCD. While the four spectral images of FIG. 6(a) are not on the same plane and thus cannot be focused on simultaneously, a solution is to use optical delay systems (not shown in FIG. 6(a)), which is technically straightforward and known to one of ordinary skill in the art. Other spectral partition schemes are also feasible, and can be designed in the spirit of this invention by those of ordinary skill in the art.

Figure 6B:
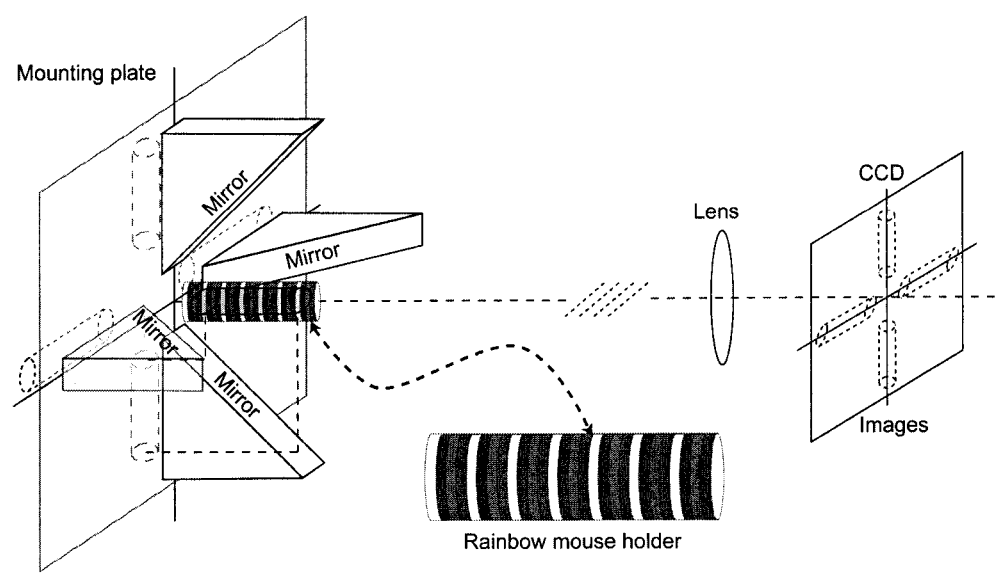
FIG. 6(b) is an illustration of an alternate exemplary MBLT system in an embodiment according to the present invention.
Figure 6C:
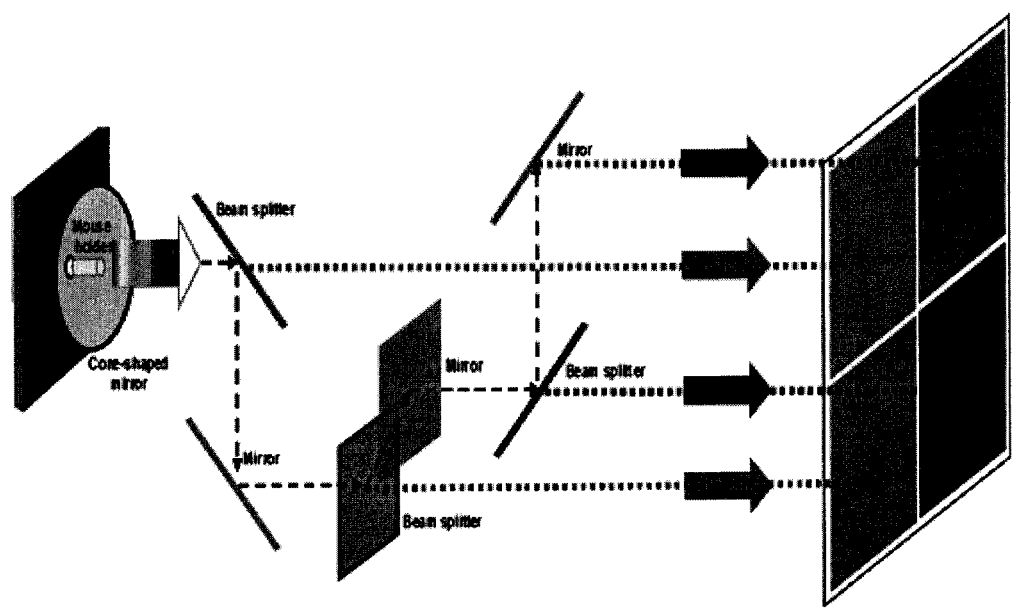
FIG. 6(c) is an illustration of another alternate exemplary MBLT system that includes a truncated cone-shaped mirror in an embodiment according to the present invention.

An alternative embodiment of a multi-view system is shown in FIG. 6(b). In this embodiment the mouse holder is comprised of colored bands of material that act as filters for the light received from the bioluminescence-emitting subject/object. Yet another embodiment of a multi-spectral subsystem is shown in FIG. 6(c). The multi-spectral BLT system of FIG. 6(c) includes a CCD camera, a truncated cone-shaped mirror with a mouse holder on its principle axis, three beam splitters with different wavelength ranges and three highly reflective mirrors. The optical path differences of the embodiment of FIG. 6(c) can be optically or digitally corrected.

C. Image Acquisition Subsystem, System Calibration and SNR

In one embodiment, a highly sensitive CCD camera is be used for image acquisition. An exemplary camera that can be used, for example, is Princeton Instruments VersArray 2048B, though others are contemplated within the scope of this invention. The CCD camera of FIG. 6(a) supports, for example, about 2048×2048 imaging pixels, 13.5×13.5 μm² pixel size, and a 16 bits dynamic range. In the spectral range 500-750 nm, quantum efficiency (QE) is higher than 80% (peak EQ>92% at 550 mm). The camera can be cooled to about −110° C. using, for example, a liquid nitrogen cooling method. At this temperature, the typical CCD read noise is about 2 electrons rms, and the dark current is less than about 1 electron per hour per pixel. The camera is coupled with a Nikon normal 50 mm f/1.2 AIS manual focus lens (Nikon Inc.), and mounted on a travel stage to adjust the focal distance. The minimum focus distance is about 50 cm with a field of view of about 25×25 cm². Since the total area of the images can be made about 24×24 cm², the system can cover all the multi-spectral signals in parallel.

The CCD camera is calibrated to remove noise and systematic biases utilizing bias frames, dark frames, and flat frames. Bias frames compensate for read-out noise and interference from the computer. Dark frames measure the dark current readout of the CCD. Flat frames correct disfigurements of the light paths and the CCD chip. After the calibration, an absolute intensity calibration of the whole imaging system is conducted to estimate the signal brightness in physical unit (Watts/cm²/sr). For that purpose, an absolutely calibrated 8-inch integrating sphere (Sphere Optics, Inc., Contoocook, N.H.) can be used along with a 4-inch sphere containing a tungsten lamp light source. A 6-position automated filter wheel with 5 filters (500 nm, 550 nm, 600 nm, 650 nm, 700 nm) and a variable attenuator with a large dynamic range are placed between the two spheres to select a particular wavelength and control the light level entering the 8-inch sphere. The 2-inch output aperture of the 8-inch sphere produces as low as $2.07 \times 10^{-13}$ Watts/cm²/sr in the spectral region of interest. By imaging this output aperture, the gray level of the CCD can be mapped into physical unit.

The signal-to-noise ratio (SNR) of a camera system such as the embodiments of the one described herein can be computed as:

$$SNR = \frac{S}{\sqrt{S + D \times t + N^2}},$$

where S is the signal per pixel in electrons, t is the integration time, D is the dark current (electrons/pixel/second), and N the CCD read noise (electrons rms/pixel). A typical way to increase SNR is to sum pixels before readout. A binning value of k means that a group of k×k pixels is combined to form one super-pixel and have k×k times the original signal and the dark current. The readout noise remains the same if a VersArray 2048B CCD with on-chip binning is used. Hence:

$$SNR_{k \times k} = \frac{S \times k \times k}{\sqrt{S \times k \times k + D \times t \times k \times k + N^2}}.$$

The trade-off of binning is spatial resolution. In BLT reconstruction, the size of each finite element can be ~1 mm. Hence, each pixel corresponds to a square of 0.12×0.12 mm² on the mouse body surface. Therefore, 8×8 binning can be used to increase SNR.

In addition to increasing the binning size, there are other ways to increase SNR. By capturing multi-view and spectrally resolved signals in parallel, there is more room to increase the integration time. In each experiment, about 5-20 minutes can be used according to the signal strength. A lens with a larger aperture can be used to increase the signal strength significantly. For example, an f/1.0 lens can increase the signal 7.8 times versus an f/2.8 lens. On the other hand, a larger aperture will reduce the depth of field and make the camera focusing more difficult. In one embodiment, an on-shelf f/1.2 lens is used. Also, increasing the mouse body temperature can increase the bioluminescent signal effectively. A biocompatible heating method can be used to improve SNR/information content.

D. Diffuse Optical Tomography (DOT) Subsystem

An embodiment of a diffuse optical tomography (DOT) subsystem (not shown in FIG. 6) utilizes a tunable laser (TOPTICA Photonics AG) with 525-700 nm wavelength range and average power of approximately 10 mW. A mirror system with rotation and translation ability scans the laser beam across the mouse body surface. Then, the multi-views of diffusive signals around the mouse can be recorded on the CCD camera. The body surface of a mouse can be reconstructed from a CT/MRI scan or other means such as optical surface mapping. Optical properties of the mouse can be reconstructed using DOT, including attenuation, scattering and anisotropy of major components such as heart, lungs, liver, stomach, bones, or their sub-regions, etc. In various embodiments, DOT can be improved utilizing image volumes/atlases obtained from micro-CT, micro-MRI and/or other modalities.

The optical parameters are reconstructed in the spectral bands of interest using classic DOT or time-resolved DOT. In this procedure, multi-excitation and multi-detection strategy can be employed to enhance numerical stability. The finite element method can be used for DOT. From the finite element theory, the diffusion equation and the boundary condition can be formulated into a finite-element-based matrix equation. An objective function is defined to measure the total variation between the model predicted photon density and measured photon density on the body surface of the mouse. The adjoint approach can be used as an effective and efficient way to calculate the gradient of the objective function. The Quasi-Newton method and an active set strategy can be used to solve the minimization problem subject to the practical constrains. Since the optical parameters can be constrained to piecewise constant variables corresponding to different organ regions, the reconstruction of optical parameters are numerically more robust, leading to an optimal mouse model for the purpose of MBLT.

System Integration

The bioluminescent imaging device and the anatomic imaging scanner, such as a micro x-ray CT scanner, can be electronically and mechanically integrated for MBLT but need not be in the same way in all embodiments. In one embodiment, the hardware structures of the two imaging units can share a table and/or a holder that can be attached to a table. This embodiment can allow the translation of an object for x-ray CT scanning to be extended into the bioluminescent imaging device in a precise and repeatable fashion. Some embodiments may be configured to optimize and integrate software packages for CT/micro-CT, MBLT, image visualization and analysis. A user interface to perform and/or to configure such functions can also be provided in some embodiments; in some such embodiments, the user interface can further allow viewing of results and may allow control of parameters with respect to such viewing, as well as iterations as defined by programmed procedures and/or based on users' interventions to perform MBLT iteratively. Any software capable of performing such functions can be implemented on one or more processing elements.

Exemplary Applications

The following applications are intended as illustrative examples only and are not limiting of the invention. According to exemplary embodiments, advanced imaging, such as lung BLT/MBLT, is enabled in that the structural and function information can be obtained concurrently with the information at the molecular/cellular level, and can be evaluated accordingly. This combination allows simultaneous examination of gene expression and anatomic structures and improves understanding of the human lungs.

Exemplary embodiments may be used in gene therapy imaging, to probe the distribution of the administered gene, reporter genes, such as those producing luciferase, can be included in the transfecting virus. These genes cause the emission of light, enabling the functional gene to be identified within the target tissue.

The embodiments described above are given as illustrative examples only. It will be readily appreciated by those skilled in the art that many deviations and other applications may be made from the specific embodiments disclosed in this specification without departing from the scope of the invention.

REFERENCES

1. Cong, A. and G. Wang, Multi-spectral bioluminescence tomography: Methodology and simulation. Int'l J. of Biomed. Imaging, 2006. ID57614: p. 1-7.
2. Wang G, Shen H, Kumar D, Qian X, Cong W X: The first bioluminescence tomography system for simultaneous acquisition of multi-view and multi-spectral data. To appear in International Journal of Biomedical Imaging, 2006
3. Han, W., W. X. Cong, and G. Wang, Mathematical study and numerical simulation of multispectral bioluminescence tomography. International Journal of Biomedical Imaging, 2006b. In process.
4. Han W M, Wang G: Theoretical and numerical analysis on multispectral bioluminescence tomography. IMA Journal of Applied Mathematics, doi:10.1093/imamat/hx1031, 1-19, 2006

The invention claimed is:

1. A method comprising:
producing first imaging data associated with an object via a first imaging technique, the first imaging data representing a first image of the object;
producing first structural model data associated with the object by processing the first image of the object, the first structural model data yielding a first structural model of the object;
obtaining wavelength-dependent spatial distributions of optical properties inside the object via optical means including diffuse optical tomography with the aid of the first image of the object or the first structural model of the object;
acquiring multi-spectral datasets from optical signals emitted from a bioluminescent source inside the object and measured at the surface of the object, and
reconstructing an underlying light-emitting bioluminescent source distribution based on the wavelength-dependent distributions of optical properties and optical measurements of said optical signals at the surface of the object.

2. The method of claim 1, further comprising reconstructing a final reconstructed image comprised of said underlying light-emitting bioluminescent source distribution mapped to said first image of the object or first structural model of the object.

3. The method of claim 2, wherein the final reconstructed image is reconstructed from multi-spectral data collected from a single angle of view or multiple angles of view.

4. The method of claim 2, wherein the final reconstructed image is reconstructed using an iterative or analytic approach.

5. The method of claim 2, wherein the final reconstructed image shows one or more of cross-sectional, volumetric or dynamic views of the object or quantitative features of underlying light-emitting source distribution of the object.

6. The method of claim 1, wherein obtaining wavelength-dependent distributions of optical properties inside the object comprises obtaining said optical properties from a database.

7. The method of claim 1, wherein the first image of the object or the first structural model of the object renders two or three dimensional structural details of the object.

8. The method of claim 1, wherein the reconstructed underlying light-emitting bioluminescent source distribution shows two-dimensional or three-dimensional distribution of a light-emitting bioluminescent source from the object, the light-emitting bioluminescent source is one of a time-dependent source of light or non-time-dependent source of light.

9. The method of claim 1, wherein the reconstructed underlying light-emitting bioluminescent source distribution is reconstructed from multi-spectral datasets due to multiple types of light-emitting bioluminescent source distributions with various spectral characteristics.

10. The method of claim 1, wherein the acquiring step comprises collecting the optical signals via one or more optical sensors.

11. The method of claim 10, wherein the acquiring step further comprises configuring optical path components in at least one optical path of the optical signals, the optical path components comprising at least a plane beam splitter, a dichroic beam splitter, and a mirror.

12. The method of claim 1, wherein the optical properties include at least one of absorption coefficients, scattering coefficients, scattering anisotropy, indices of refraction, and features of underlying sources.

13. The method of claim 1, wherein the first imaging technique or first image processing procedure includes at least one of x-ray CT, micro-CT, magnetic resonance imaging, ultrasound, surface imaging, and digital atlas matching.

14. The method of claim 1, wherein the optical properties comprise one or more of absorption coefficients, scattering coefficients, scattering anisotropy, indices of refraction, and features of underlying light-emitting sources.

15. A multi-spectral bioluminescence tomography (MBLT) system comprising:
a multi-view subsystem comprising a plurality of mirrors configured to produce a respective plurality of views of an object on a plane, the plurality of mirrors mounted symmetrically about the object;
an image acquisition subsystem configured to yield imaging data of an object, the image acquisition subsystem comprising a camera focused on the plane;
an optics subsystem configured to obtain wavelength-dependent distributions of optical properties inside the object, the optics subsystem having at least one optical sensor including the camera;
a multi-spectral subsystem configured to acquire multi-spectral datasets from optical signals emitted from the object, the optical signals comprising bioluminescence signals in a spectral range, and the multi-spectral subsystem comprising
a first dichroic beam splitter that reflects a first portion of the bioluminescence signals in the spectral range directly onto the camera and transmits a second portion of the bioluminescence signals in the spectral range to a second dichroic beam splitter,
the second beam splitter reflects a third portion of the bioluminescence signals in the spectral range directly onto the camera and transmits a fourth portion of the bioluminescence signals in the spectral range to a mirror,
the mirror reflects the fourth portion of the spectral range to the camera; and
a reconstruction engine configured to reconstruct an underlying light-emitting bioluminescent source distribution based on the wavelength-dependent distributions of optical properties.

* * * * *